United States Patent [19]

Malmros

[11] 4,444,892
[45] * Apr. 24, 1984

[54] ANALYTICAL DEVICE HAVING SEMICONDUCTIVE ORGANIC POLYMERIC ELEMENT ASSOCIATED WITH ANALYTE-BINDING SUBSTANCE

[76] Inventor: Mark K. Malmros, P.O. Box 106, Washington Crossing, Pa. 18977

[*] Notice: The portion of the term of this patent subsequent to Jun. 15, 1999 has been disclaimed.

[21] Appl. No.: 378,399

[22] Filed: May 17, 1982

Related U.S. Application Data

[63] Continuation-in-part of Ser. No. 198,782, Oct. 20, 1980, Pat. No. 4,334,880.

[51] Int. Cl.³ .................... G01N 27/12; G01N 33/54
[52] U.S. Cl. .................... 436/528; 324/71.5; 422/68; 435/7; 436/151; 436/531; 436/806; 436/827
[58] Field of Search ............. 436/518, 531, 528, 531, 436/806, 827; 324/71 SN

[56] References Cited

U.S. PATENT DOCUMENTS

| | | | |
|---|---|---|---|
| 3,932,807 | 1/1976 | Wilson | 324/71 SN |
| 3,999,122 | 12/1976 | Winstel | 324/71 SN |
| 4,103,227 | 7/1978 | Zemel | 324/71 SN |
| 4,180,771 | 12/1979 | Guckel | 324/71 SN |

Primary Examiner—Sidney Marantz
Attorney, Agent, or Firm—Omri M. Behr

[57] ABSTRACT

A method, sensor and semiconductor device for determining the concentration of an analyte in a medium. The device features an element constructed of semiconductive organic polymer associated with a binding substance having specific affinity for the analyte.

9 Claims, 4 Drawing Figures

ANALYTICAL DEVICE HAVING SEMICONDUCTIVE ORGANIC POLYMERIC ELEMENT ASSOCIATED WITH ANALYTE-BINDING SUBSTANCE

RELATED APPLICATIONS

This application is a continuation-in-part of my copending application Ser. No. 198,782 filed Oct. 20, 1980 now U.S. Pat. No. 4,334,880 granted June 15, 1982.

BACKGROUND OF THE INVENTION

Immunoassays have been used routinely for the indentification and quantitation of haptens, antigens and antibodies (all broadly termed analytes). The basic principle of all immunoassays is predicated on the specific binding between components of a reaction pair (e.g. antigen/antibody, hapten/antibody, etc.) where, in some cases, one component is labeled in such a fashion as to be easily analyzed by some external means.

Radioimmunoassay (RIA) is based on the use of a radioisotope as a label for one of the components of a specific binding pair. A radioisotopically labeled component can then be detected by counting the radiation emitted by the isotope using a suitable instrument.

Other methods of labeling one component of a specific binding pair have been developed. The use of enzyme and fluorescent labels have recently been employed and are termed enzyme immunoassay (EIA) and fluorescent immunoassay (FIA) respectively. Again, with the use of suitable reagents and instruments, these labels can be used for the determination of analytes in a liquid medium. Many variations to the basic procedures are in use, but most require the steps of reaction, separation, and detection of label.

More recently, electrochemical sensors have been employed in an effort to simplify and/or improve the sensitivity of these procedures. Basically, they employ an ion selective electrode to detect the reaction product of an enzyme which has been used as a level for one component of a specific binding pair.

The present invention seeks to eliminate the preparation of a labeled component of a specific binding pair, the separation of such a component from the assay system, as well as its subsequent detection; thereby greatly simplifying the method of performing an immunoassay. More specifically, the present invention relates to a new and useful improvement in a method for the determination of analytes in a liquid medium by the use of a biochemically sensitive semiconductor device set forth in the following description and specifications.

SUMMARY OF THE INVENTION

The present invention relates to a device to be used in a method for the determination of analytes in a liquid medium. More specifically, the present invention relates to a device, composed of an electrically semiconductive material suitably a semiconductive organic polymer to which an analyte specific binding substance is suitably immobilized to said material in such a fashion that the binding of said analyte to its specific binding substance alters the electrical semiconductive properties of the semiconductive material in a measureable way. Further, the present invention relates to a method of determining the presence of an analyte in a liquid medium using such a device.

As most specific binding substances for any particular analyte are biological in origin, said device is termed a biochemically sensitive semiconductor device or BSSD. These specific binding substances are generally of an organic chemical nature, displaying certain measureable porperties of which one is a specific electrical charge. Furthermore, for a specific binding substance, its electrical charge will vary as a result of its binding to its particular analyte; an example of a binding substance and its specific analyte is an antibody and its specific antigen. In accordance with this invention the binding of an antigen (analyte) by its specific antibody (binding substance) may be determined by detecting and measuring the change in the electrical charge of one or both elements of the binding reaction. By placing either one of the two elements of a specific binding system in close proximity to a material which can be influenced by the field of the electrical charge, a change in that electrical field as a result of the binding reaction will effect a change in the properties of that material. If the properties of this material are measureable, it follows that the binding reaction is also measureable.

DETAILED DESCRIPTION OF THE INVENTION

Figure 1:
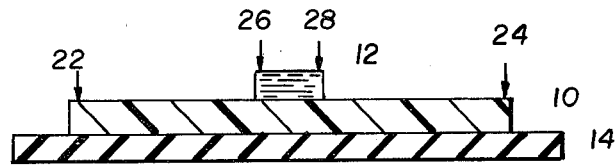
FIG. 1 is a schematic cross-sectional elevational view of the element portion of the device.
Figure 3:
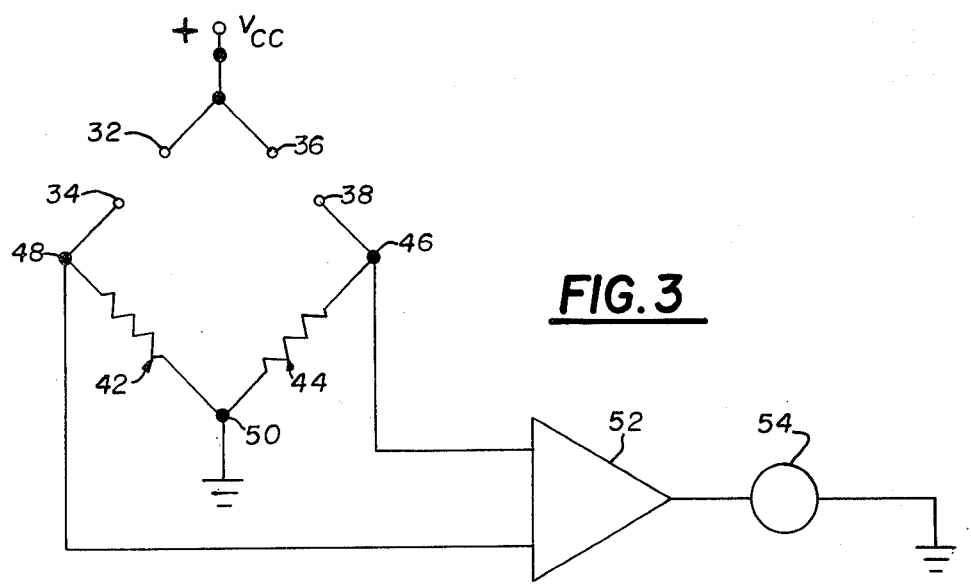
FIG. 3 is a circuit diagram for operation of the device.
Figure 2:
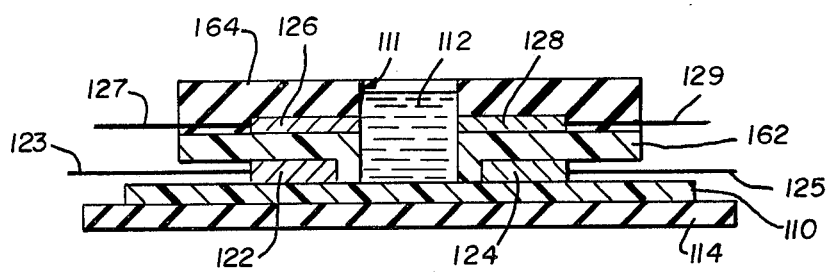
FIG. 2 is a further embodiment of FIG. 1.
Figure 4:
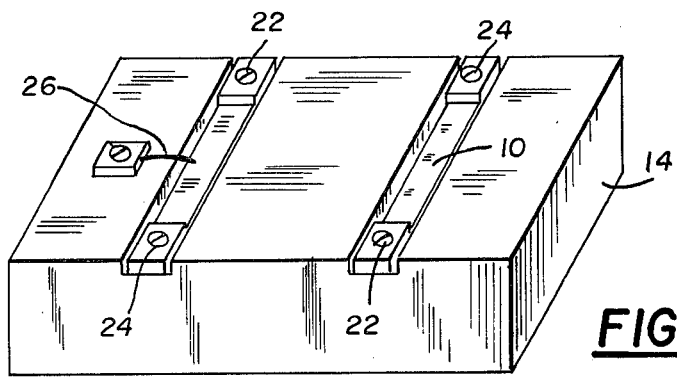
FIG. 4 is a perspective plan view of an embodiment of the carrier portion of the device.

The invention and its operation may be best described by referring separately to the element portion as illustrated in FIGS. 1, 2 and 4 and the electrical operation of the device as illustrated in FIG. 3.

The central element 10 of the device comprises a strip of semiconductive organic polymer. Any semiconductive organic polymer may be utilized. This rather novel class of compounds includes polyacetylene, poly(p-phenylene), polypyrorle, poly(polyalkapolydiynes) such as poly(hepta-1,6-diyne), poly (p-phenylenesulfide), polymetallophthalocyanines, suitably polyaluminophthalocyanine fluoride and polyphthalocyanine silorane. This listing of semiconductive organic polymers is not to be considered as limiting but merely illustrative.

The organic polymers set forth above may be utilized either in the undoped condition or containing conventionally employed dopants, for example, arsenic pentafluoride, iodine, perchlorate, and the like.

The element 10 is exposed to a binding agent. It is generally sufficient to soak the element in an aqueous solution of the binding agent in a suitable bufer. The term "binding agent" in this context is understood to include any material which will undergo a coupling reaction of the type generally understood in biochemistry to be of the antigen/antibody reaction.

Illustrative of binding agents are antibody to IgG, enzymes such as B-galactosidase, concanavalin A, limulin, cofactor type enzymes such as isocitrate dehydrogenase, alcohol dehydrogenase, NAD (nicotinamide adenine dinucleotide), enzyme substrates such as isocitrate enzymes inhibitors such as, B-galactosidase inhibitors hormones such as thyroxine, enzyme substrate analosgs, such as O-nitrophenyl-B-D-galactopyranoside antigens such as human chorionic gonadotropin Again these illustrations are not to be considered as critical or limiting.

While the illustrations of the present invention disclose the simple contact treatment of the binding agent with the polymeric element, it will be understood by those skilled in the art that under certain circumstances an activating treatment of the substrate of the element 10 may be necessary to bind to certain binding agents, such reactions generally are conventional and are well known to those skilled in the art and are included within the scope of the present invention.

In the normal course of treatment of the element 10 with the binding agent, freshly synthesized polymer is placed in a suitable buffer containing the solution of the desired binding agent, incubated at room temperature from about 8 to about 24 hours, washed with saline solution and stored under nitrogen. While nitrogen storage is not entirely necessary it has been found that many binding agents are sensitive to oxygen and their activity is best preserved by reducing possible exposure to this substance.

The schematic representation of the central portion of the device is shown in FIG. 1 wherein element 10 comprising the semiconductive material and the binding agent associated therewith are mounted on an insulating material 14. There are applied to element 10 electrical contacts 22 and 24. When the device is in operation and the analyte solution 12 is placed thereon, additional electrical contacts 26 and 28 are applicable to medium 12. This can be noted by reference to FIG. 4 showing at the right hand portion thereof the location of contacts 22 and 24 in relationship to element 10 and insulating carrier 14. At the right hand side thereof it is shown a similar arrangement showing contact 26. Contact 28 could be similarly applied. It is particularly preferred for reasons of good connection that the contacts be gold plated or of gold wire.

Where it is desired to utilize the full potential of the apparatus a slightly more complex arrangement as illustrated in FIG. 2 may be employed. The last two digits of the item numbers correspond to the appropriate two digit numbers in FIG. 1.

Thus, FIG. 2 illustrates a base 114 carrying element 110 comprising the semiconductive organic polymer and the binding agent. Upon the other surface of the element 110 are placed a pair of metallic contacts 122 and 124 having the leads 123 and 125 respectively connected thereto. The lower portion of a well is created by disc shaped insulating elements 162 having the illustrated L shaped cross section. Over disc element 162 positioned to be on opposite sides of a well 111 are electrodes 126 and 128 having leads 127 and 129 respectively attached thereto. These contacts 126 and 128 comprise only a very small portion of the wall area of the well and are surrounded by insulating disc element 164 medium containing the analyte 112 is placed in the thus produced well 111.

The device is conventionally operated in the Wheatstone Bridge circuit illustrated in FIG. 3. In this circuit a positive potential is applied between contact points 32 and 36. One element 10 is connected between contacts 32 and 34 and a similar element is connected between contacts 36 and 38. Contact 34 is connected to a junction 48 to which is connected one end of resistor 42 which may, if desired, be a variable resistor. Similarly, one end of another resistor 44 which may also be a variable resistor is connected at junction point 46 to which contact 38 is also connected. Junctions 46 and 48 are connected to a differential amplifier 52 which is connected to ground through a meter device 54.

In the operation of the device the two elements 10 connected to 32/34 and 36/38 respectively are balanced in the conventional manner. Medium containing the analyte is then placed, say, in well 111 and the change in resistance of that particular element is measured. It has been found that the change in resistance is a factor of time and concentration and thus calibration in a standard solution is desirable. Further it is possible to increase the sensitivity of the measurement by applying a potential to either contact 26 or contact 28 or, if the potential is equal, to both at the same time. If desired, contacts 26 and 28 maybe utilized to measure the conductivity of the medium in a conventional manner.

The term "analyte" as used herein refers to antigens, antibodies, haptens, enzymes, enzymes substrates, enzyme substrates analogs, agglutinins, lectin, enzyme cofactors, enzyme inhibitors, hormones and the like.

EXPERIMENTAL

Preparation A

The IgG fraction of goat anti-rabbit IgG serum was isolated by a combination of 33% ammonium sulfate precipitation and DEAE cellulose chromatography as described by Garvey, J. S. et al (1980) in *Methods in Immunology*, pp. 193-198, W. A. Benjamin Inc. Further specific purification, as necessary, was effected by the technique of affinity chromatography, various procedures of which are described in the literature.

Preparation AA

The trans-polymer of acetylene was prepared, using a Zeigler-type catalyst, following the procedure of Ito et al., Journal of Polymer Science, 12,11, (1974).

Preparation BB

Poly (p-phenylene) is prepared by the procedure of Shacklette et al Syn. Met. 1, 307 (1980).

Preparation CC

Poly-pyrole is prepared by the procedure of Kanazawa et al Syn. Met. 1, 329 (1980).

Preparation DD

Poly(hepta-1-,6-diyne) is prepared by the method of Gibson, et al, J.Chem.Soc. (Chem. Comm) 426, (1980).

Preparation EE

Poly (P-phenylenesulfide) Hexafluroarsenate is preared by the method of Rabolt et al, J.Chem Soc. (Chem Comm.) 347, (1980).

EXAMPLE I

Strips of freshly synthesized polyacetylene, approximately 4×20 mm, were placed in a 0.05 M carbonate-bicarbonate buffer, pH 9.5 containing 5 mg/ml of purified goat anti-rabbit IgG and incubated overnight at room temperature. The polyacetylene antibody strips were subsequently washed with a saline solution and stored under nitrogen.

EXAMPLE II

Strips of freshly synthesized poly(p-phenylene), approximately 4×20 mm, are placed in a 0.05 M carbonate-bicarbonate buffer, pH 9.5 containing 5 mg/ml of monoclonal antibody to human chorionic gonadotropin and incubated overnight at room temperature. The poly(p-phenylene) strips are subsequently washed with a saline solution and stored under nigrogen.

EXAMPLE III

Strips of freshly synthesized polypyrrole, aporoximately 4×20 mm, are placed in a 0.05 M carbonate-bicarbonate buffer, pH 9.5 containing 5 mg/ml of avidin and incubated overnight at room temperature. The Polypyrrole/avidin strips are subsequently washed with a saline solution and stored under nitrogen.

EXAMPLE IV

Strips of freshly synthesized poly(hepta-1-, 6-diyne), approximately 4×20 mm, are placed in a 0.05 M carbonate-bicarbonate buffer, pH 9.5 containing 5 mg/ml of B-galactosidase and incubated overnight at room temperature. The poly(hepta-1-, 6-diyne)/B-galactosidase strips are subsequently washed with a saline solution and stored under nitrogen.

EXAMPLE V

Strips of freshly synthesized poly(p-phenylene sulfide)Hexafluroarsenate, approximately 4×20 mm, are placed in a 0.05 M carbonate-bicarbonate buffer, pH 9.5 containing 5 mg/ml of linulin and incubated overnight at room temperature. The poly(p-phenylene sulfide)-Hexafluroarsenate/linalin strips are subsequently washed with a saline solution and stored under nitrogen.

EXAMPLE VI

Strips of freshly synthesized polyaluminothalocyanime fluoride, approximately 4.20 mm, are placed in a 0.05 M carbonate-bicarbonate buffer, pH 9.5 containing 5 mg/ml of NAD and incubated overnight at room temperature. The polyaluminothalocyanime fluoride strips are subsequently washed with a saline solution and stored under nitrogen.

EXAMPLE VII

A pair of elements prepared in accordance with example I but connected into a pair of devices in accordance with the right hand portion of the device illustrated in FIG. 4 and connected into the circuit of FIG. 2. The bridge circuit was brought into balance and 10 microliters of rabbit IgG in PBS buffer (500 micrograms of IgG/ml were placed on one element and the same volume of PBS buffer on the other element taking care to avoid contact of either sample with the metallic contact elements 22 and 24 respectively. Element 44 in the circuit is a variable transformer and readings were taken from T=0 to T=1 hour as follows:

| T = 0 | 470 |
| T = 1 min | 498 |
| T = 2 min | 488 |
| T = 3 min | 563 |
| T = 9 min | 731 |
| T = 20 min | 687 |
| T = 1 hr | 587 |

The supply voltage was 5.1 volts.

The experiment was repeated using 20 microliters of IgG with a supply voltage of 5.0 volts and the following readings obtained:

| T = 0 | 378 |
| T = 1 | 358 |
| T = 5 | 403 |
| T = 10 | 499 |
| T = 20 | 499 |
| T = 30 | 435 |

EXAMPLE VIII

As in Example I, a strip of polyacetylene-antibody was prepared, using a goat anti-rabbit IgG preparation, and placed in a teflon holder. A mesh with a 3 mm diameter cutout was placed over the polyacethylene film and used to overlay an aqueous gelatin film, taking the precaution not to physically or electrically connect the two conductive clamps with the gelatin film. A measurement of the specific analyte was made with this device as described in Example VII.

EXAMPLE IX

As in Example II, a strip of polyacetylene-antibody gelating film was prepared except that a third electrical connection was formed by placing a piece of platinum wire just on the surface of the gelatin film. In this exammple, the device is similar in principle to a field effect transistor. This third electrical connection allows for the application of an elctrical potential at a right angel to the flow of electrons through the polyacetylenne-antibody film. Using this device, the binding of rabbit IgG to goat anti-rabbit IgG antibody was ascertained as described in Example VII.

The procedures of the proceeding Examples were repeated utilizing a device of FIG. 2 wherein 2 to 10 volts are applied to contact 126 in the device.

EXAMPLE X

The invention being thus described, it will be obvious that the same may be varied in many ways. Such variations are not to be regarded as a departure from the spirit and scope of the invention, and all such modifications are to be included within the scope of the following claims.

I claim:

1. A variable resistance sensor for the determination of an analyte in a medium comprising:
   (a) an insulating structure,
   (b) element means having an active part comprised of semiconductive organic polymer of polyacetylene including a specific binding substance for the analyte, mounted on said structure for exposure to the medium and
   (c) electrodes positioned to contact the element.

2. The sensor as in claim 1 wherein there are four electrodes.

3. The sensor as in claim 1 where there are two electrodes.

4. The sensor as in claim 1 where there are three electrodes.

5. The sensor as in claims 1 or 4 wherein the specific binding substance is selected from the group consisting of antibodies, antigens, enzymes, enzyme substrates, analogs of enzyme substrates, agglutinins, lectins, enzyme cofactors, enzyme inhibitors and hormones.

6. A method of identifying the type and quantity of an analyte in a medium comprising the steps of:
   (a) preparing an element of semiconductive organic polymer of polyacetylene
   (b) treating the element with a specific binding substance,
   (c) exposing the element to the medium,
   (d) measuring the change in an electrical characteristic of the treated element.

7. The method of claim 6 including the steps of applying at least two electrodes to contact the element and measuring the electrical changes between the electrodes.

8. The method of claim 7 including the step of applying three electrodes to contact the element.

9. The method of claims 6, 7 or 8 where the specific binding substance is selected from the group consisting of an antibody, an antigen, an enzyme, an enzyme substrate, an enzyme substrate analog, an agglutinin or lectin, an enzyme cofactor, an enzyme inhibitor and a hormone.

* * * * *